United States Patent
Guo et al.

(10) Patent No.: US 11,678,971 B2
(45) Date of Patent: Jun. 20, 2023

(54) STENT GRAFT USED FOR INTERVENTIONAL TREATMENT OF ABDOMINAL AORTIC DISEASES

(71) Applicant: HANGZHOU ENDONOM MEDTECH CO. LTD., Zhejiang (CN)

(72) Inventors: Wei Guo, Zhejiang (CN); Yongsheng Wang, Zhejiang (CN); Anwei Li, Zhejiang (CN)

(73) Assignee: HANGZHOU ENDONOM MEDTECH CO. LTD. HANGZHOU, CHINA, Hangzhou (CN)

( * ) Notice: Subject to any disclaimer, the term of this patent is extended or adjusted under 35 U.S.C. 154(b) by 0 days.

(21) Appl. No.: 16/958,328

(22) PCT Filed: Dec. 27, 2018

(86) PCT No.: PCT/CN2018/124414
§ 371 (c)(1),
(2) Date: Jun. 26, 2020

(87) PCT Pub. No.: WO2019/129151
PCT Pub. Date: Jul. 4, 2019

(65) Prior Publication Data
US 2021/0052364 A1    Feb. 25, 2021

(30) Foreign Application Priority Data
Dec. 29, 2017   (CN) .......................... 201711480151.1

(51) Int. Cl.
*A61F 2/07*         (2013.01)
*A61F 2/954*        (2013.01)
(Continued)

(52) U.S. Cl.
CPC ........ *A61F 2/07* (2013.01); *A61F 2220/0041* (2013.01); *A61F 2230/001* (2013.01)

(58) Field of Classification Search
CPC .. A61F 2/07; A61F 2/2418; A61F 2220/0075; A61F 2/954; A61F 2/848;
(Continued)

(56) References Cited

U.S. PATENT DOCUMENTS 5,976,179 A * 11/1999 Inoue ........................ A61F 2/07
                                                        623/1.36
8,474,120 B2 * 7/2013 Hagaman .................. A61F 2/07
                                                         29/458
(Continued)

FOREIGN PATENT DOCUMENTS

CN       201333254 Y      10/2009
CN       102415924 A       4/2012
(Continued)

OTHER PUBLICATIONS

International Search Report issued in International Application No. PCT/CN2018/124414, dated Mar. 27, 2019, pp. 1-6, State Intellectual Property Office of the P.R. China, Beijing, China.
(Continued)

*Primary Examiner* — Ann Schillinger
(74) *Attorney, Agent, or Firm* — Hauptman Ham, LLP (57) ABSTRACT

The invention discloses a stent graft used for interventional treatment of abdominal aortic disease, comprising a tube body composed of a tubular covering and a plurality of annular stents, and the tube body comprises a first tube body and a second tube body that arranged in sequence from the proximal end to the distal end, wherein the diameter of the first tube body is greater than diameter of the second tube body; the first tube body and the second tube body are connected by a transition section as a whole; the diameter at central part of the transition section is smaller than the diameter of the proximal end of the transition section and the diameter of the distal end of the transition section; a plurality of fenestrations are disposed on the first tube body and the (Continued)

transition section. The invention provides a stent graft having a smaller diameter of the portion near the branch vessels or branch stents after released, and has more space for accommodating branch vessels or branch stents for interventional treatment of abdominal aortic diseases.

19 Claims, 5 Drawing Sheets

(51) Int. Cl.
*A61F 2/962* (2013.01)
*A61F 2/86* (2013.01)
*A61F 2/95* (2013.01)
*A61F 2/06* (2013.01)

(58) Field of Classification Search
CPC .. A61F 2/9522; A61F 2002/9665; A61F 2/06; A61F 2/2409; A61F 2002/067; A61F 2002/075; A61F 2002/9511; A61F 2250/006; A61F 2002/061
See application file for complete search history.

(56) References Cited

U.S. PATENT DOCUMENTS

| | | | |
|---|---|---|---|
| 2005/0010277 A1* | 1/2005 | Chuter | A61F 2/064 623/1.13 |
| 2005/0102018 A1* | 5/2005 | Carpenter | A61F 2/07 623/1.11 |
| 2010/0249899 A1* | 9/2010 | Chuter | A61F 2/07 623/1.13 |
| 2013/0282102 A1* | 10/2013 | Peterson | A61F 2/07 623/1.13 |
| 2013/0289702 A1* | 10/2013 | Coghlan | A61F 2/07 623/1.13 |
| 2013/0296998 A1* | 11/2013 | Leotta | G05B 15/02 623/1.11 |
| 2014/0148888 A1* | 5/2014 | Barrand | A61B 17/12131 623/1.2 |
| 2014/0180393 A1* | 6/2014 | Roeder | A61F 2/06 623/1.15 |
| 2015/0157477 A1 | 6/2015 | Shahriari | |
| 2016/0081787 A1* | 3/2016 | Parodi | A61F 2/07 623/1.13 |
| 2016/0120667 A1* | 5/2016 | Bolduc | A61F 2/89 623/1.13 |
| 2016/0310216 A1* | 10/2016 | Van Bibber | A61B 34/10 |
| 2017/0290654 A1* | 10/2017 | Sethna | A61F 2/07 |
| 2019/0021887 A1* | 1/2019 | Roeder | A61F 2/852 |

FOREIGN PATENT DOCUMENTS

| | | |
|---|---|---|
| CN | 206761796 U | 12/2017 |
| EP | 2740441 A1 | 6/2014 |
| EP | 2815722 A1 | 12/2014 |
| WO | 2010105195 A2 | 9/2010 |
| WO | 2012058582 A1 | 5/2012 |

OTHER PUBLICATIONS

Extended European Search Report issued in corresponding EP Application No. EP 18896687.3, dated Jan. 11, 2021.

* cited by examiner

STENT GRAFT USED FOR INTERVENTIONAL TREATMENT OF ABDOMINAL AORTIC DISEASES

RELATED APPLICATION

The present application is a U.S. National Phase of International Application Number PCT/CN2018/124414, filed Dec. 27, 2018, which claims priority to Chinese Patent Application No. 201711480151.1, filed Dec. 29, 2017.

TECHNICAL FIELD

The invention relates to the technical field of medical devices, and particularly relates to a stent graft, in particular to a stent graft used for interventional treatment of abdominal aortic diseases.

BACKGROUND

Abdominal aortic aneurysm (AAA) is a common aortic disease. Epidemiological studies have shown that the incidence of abdominal aortic aneurysm in men is 5%, but in patients at the age of 80 years and over, the incidence increases to 10%, and the risk of tumor rupture is higher than other populations. It is predicted that by 2020 China's population over 80 years old will reach 30 million, and population over 90 years old will exceed 12 million. In the future, more and more advanced aged AAA patients will need treatment.

The existing main methods of treating abdominal aortic aneurysms include traditional open surgery and endovascular repair of abdominal aortic aneurysms, each of which has its own advantages. Since the first case of endovascular repair of abdominal aortic aneurysm was reported in the 1990s, it has developed rapidly in just 20 years for its advantages such as low trauma, short operation and hospital stay, fast postoperative recovery, and low perioperative mortality and complications rate.

The biggest advantage of endovascular repair surgery of abdominal aortic aneurysm is that it does not require thoracotomy or laparotomy, and does not require clamping to block blood vessels, with no ischemia of internal organs and fewer complications during the operation. However, the biggest limitation is that the visceral aorta cannot be covered, especially the superior mesenteric artery and renal artery, and it is still difficult to endovascular repair the abdominal aortic aneurysm involving the renal artery.

At present, the use of "fenestrated stent blood vessels" to implement stent blood vessel implantation treatment for such patients, that is, implanting a main body stent in the abdominal aorta, disposing a fenestration in the main body stent, and then installing a branch stent vessel in the fenestration to the branch blood vessels. The stent-type blood vessel implanted for the endovascular treatment of abdominal aortic aneurysm involves the reconstruction of the four branch arterial blood vessels of the celiac trunk artery, superior mesenteric artery, and left and right renal arteries. However, in actual operation, there are individual differences in the spatial positions of these four visceral arteries in different patients. The implantation of fenestrated stent blood vessels requires accurate detection and positioning of each patient's lesion and peripheral blood vessels, and stent blood vessels are designed and produced according to the detection results. The detection, design, and production for individual patient are not only complicated in procedures, but also affected by the precision of the instrument and the proficiency of the operator. The stent vessels produced often have poor accuracy, which greatly reduces the therapeutic effect.

On the other hand, in the release process of current stent, especially in the blood vessel segment of lesion with a more complicated shape, some stents have displacement or inaccurate positioned during the release process, which leads to problems such as endoleak after release and blocking branch vessels, and even cause a medical accident such as paraplegia or death, which not only failed to achieve the desired therapeutic effect, but also caused a large adverse effect on the patient's body and mind.

SUMMARY

The technical problem to be solved by the present invention is to provide a stent graft after released that has a smaller diameter of the portion near the branch section and has more space for accommodating branch vessels stents for interventional treatment of abdominal aortic diseases.

The technical solution adopted by the present invention to solve its technical problems is:

A stent graft used for interventional treatment of abdominal aortic disease, comprising a tubular body composed of a tubular covering and a plurality of annular stents, and the tubular body comprises a first tube body and a second tube body that arranged in sequence from the proximal end to the distal end, and the diameter of the first tube body is greater than the diameter of the second tube body;

the first tube body and the second tube body are connected by a transition section as a whole; the diameter at central part of the transition section is smaller than the diameter of the proximal end and the diameter of the distal end of the transition section;

a plurality of fenestrations are disposed on the first tube body and the transition section.

Further, in the stent graft used for interventional treatment of abdominal aortic disease, preferably the fenestrations comprise front wall fenestrations and side wall fenestrations; the front wall fenestrations are arranged on the front wall of the covering, and the side wall fenestrations are arranged on the side wall of the covering.

Further, in the stent graft used for interventional treatment of abdominal aortic disease, preferably at least two front wall fenestrations are arranged, and all of the front wall fenestrations are on the same axis, and at least one front wall fenestration is on the first tube body.

Further, in the stent graft used for interventional treatment of abdominal aortic disease, preferably the side wall fenestrations are arranged on each of two side wall surfaces of the covering, and the two side wall fenestrations are located at the same height.

Further, in the stent graft used for interventional treatment of abdominal aortic disease, preferably at an inner wall surface or at an outer wall surface of the covering, at least one support rod arranged in the axial direction is fixed to at least the proximal end of the first tube body along the circumferential direction of the covering.

Further, in the stent graft used for interventional treatment of abdominal aortic disease, preferably the support rod is fixed on the wall surface of the covering by sewing, heat sealing or bonding.

Further, in the stent graft used for interventional treatment of abdominal aortic disease, preferably at least one fixing point for fixed connection with the covering is arranged on the support rod, and the fixing point is a connection hole or an opening slot with an opening arranged on the support rod.

Further, in the stent graft used for interventional treatment of abdominal aortic disease, preferably the support rod is arranged parallel to the central axis of the stents; or a plurality of support rods are arranged in a shape of a figure eight expressed in Simplified Chinese or a shape of an inverted figure eight expressed in Simplified Chinese.

Further, in the stent graft used for interventional treatment of abdominal aortic disease, preferably connectors for a release guide wire to pass through, are arranged axially from the proximal end to the distal end on the covering, and the connectors are arranged at least two columns axially at interval.

Further, in the stent graft used for interventional treatment of abdominal aortic disease, preferably the connector is a closed-loop structure or an open-loop structure for the release guide wire to pass through or wind around; the closed-loop structure is a through hole on the connector for the release guide wire to pass through, or a through hole or a gap surrounded by the connector cooperated with the covering for the release guide wire to pass through, and the open-loop structure has a limit groove for the release guide wire to pass through.

Further, in the stent graft used for interventional treatment of abdominal aortic disease, preferably the connector with the closed-loop structure is a coil fixed on the outer wall surface of the covering; or, the connector with the closed-loop structure is a piece of wire fixed axially with spacing, and a gap that formed between the wire and the covering for the release guide wire to pass through; or the connector with the closed-loop structure is a through hole formed in the covering; or, the connectors with the open-loop structure are at least two columns of flexible connection buckles with a limit groove, the openings of the limit grooves in different columns arranged in the opposite direction.

Further, in the stent graft used for interventional treatment of abdominal aortic disease, preferably at least one axially arranged support rod is fixed at the inner wall surface or the outer wall surface of the covering, and a connector for the release guide wire to pass through is arranged at the support rod or the covering corresponding to the support rod.

Further, in the stent graft used for interventional treatment of abdominal aortic disease, preferably the first tube body, the second tube body, and the transition section are all composed of tubular covering and annular stents.

Further, in the stent graft used for interventional treatment of abdominal aortic disease, preferably a bare stent is arranged at the proximal end of the first tube body, and a plurality of barbs folded outwards are arranged at the bare stent, wherein the free end of the barbs are towards the distal end of the stent.

Further, in the stent graft used for interventional treatment of abdominal aortic disease, preferably the transition section comprises three parts in sequence, which are a proximal extension section connected to the first tube body, a transition body section, and a distal extension section, wherein the transition body section has the smallest diameter among the three parts.

Further, in the stent graft used for interventional treatment of abdominal aortic disease, preferably the transition body section is an isodiametric structure, and the proximal extension section and the distal extension section are non-isodiametric structures.

The stent graft of the present invention is a dumbbell-shaped structure with a thin center section and two thick ends, wherein the diameter of the first tube body is greater than the diameter of the second tube body, and the central diameter of the transition section is smaller than the diameter of the proximal end of the transition section and the diameter of the distal end of the transition section; the stent graft of the present invention is able to realize the endovascular repair of the abdominal aortic aneurysm involving the renal artery, and the transition body section has the smallest diameter, which can provide rich space for implanting stent in the renal artery branch, and will not squeeze the branch vessel. On the other hand, the first tube body and the transition section are provided with multiple fenestrations for anastomosis and communication with the celiac trunk artery, superior mesenteric artery, and left and right renal arteries, respectively. The fenestrations provided on the front wall and side wall of the stent graft will not cover the superior mesenteric artery and the celiac trunk artery.

In addition, connectors for a release guide wire to pass through, are arranged axially from the proximal end to the distal end on the covering, and the connectors are arranged at least two columns axially with spacing. The connectors cooperates with the release guide wire to constrain the radial dimension of the stents, so that the stents present a semi-deployed state; the diameter of the stents in the semi-deployed state is smaller than the diameter of the blood vessel, and the position can be adjusted by free rotation and longitudinal movement in the blood vessel, facilitating an accurate positioning of the stents during the release process.

Furthermore, at least one support rod is arranged at the rear wall of the covering, the support rod can be used as a stud during the assembly of the stent graft, which can not only ensure the stability of the stents during assembly, but also ensure a semi-deployed state of stable circumferential structure after the stents are partially released.

BRIEF DESCRIPTION OF THE ACCOMPANYING DRAWINGS

The present invention will be further described below with reference to the drawings and embodiments. In the drawings.

DETAILED DESCRIPTION OF ILLUSTRATED EMBODIMENTS

In order to have a clearer understanding of the technical features, purposes and effects of the present invention, the specific embodiments of the present invention will now be described in detail with reference to the drawings.

In the present invention, the "proximal end" refers to the portion of the stent or stent component that near the patient's heart along the direction of blood flow, and the "distal end" refers to the portion of the stent or stent component that away from the patient's heart.

Front and rear definition: stent tubular surface with the fenestration is the front wall, and the stent tubular surface opposite the fenestration is the rear wall, and the tubular surfaces of the stent between the front and rear walls are the side walls.

Figures 1, 2, 3:
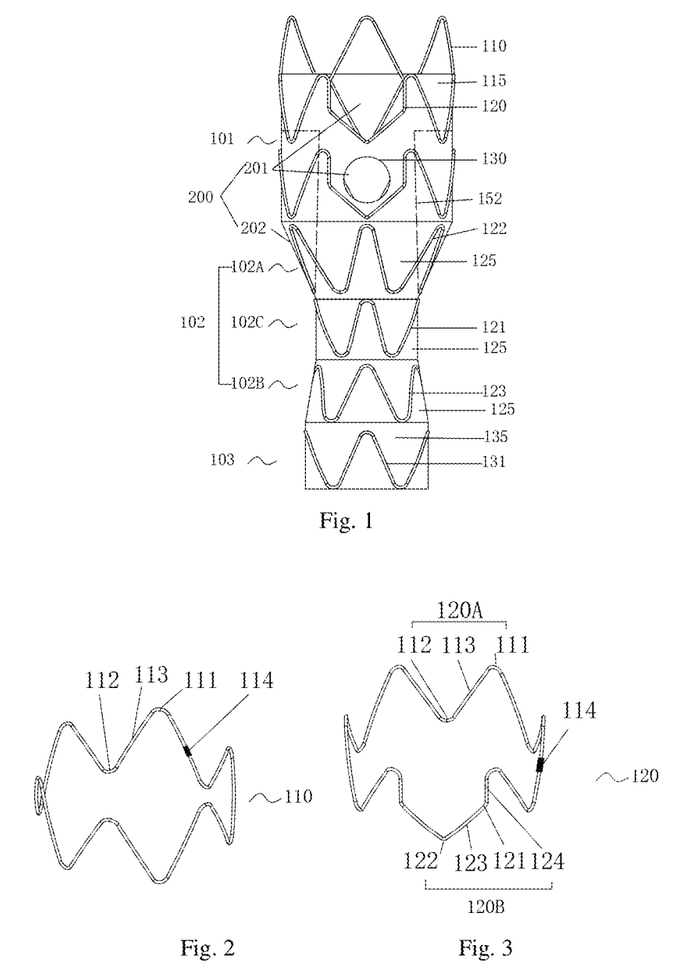
FIG. 1 is a schematic structural view of a stent graft according to the Embodiment 1 of the present invention.
FIG. 2 is a schematic structural view of a single-ring annular stent in the first tube body of Embodiment 1 of the present invention.
FIG. 3 is a schematic structural view of a fenestrated annular stent in the first tube body of Embodiment 1 of the present invention.

Embodiment 1, as shown in FIG. 1, a stent graft used for interventional treatment of abdominal aortic disease, comprises a tube body composed of a tubular covering and a plurality of annular stents, and the tube body comprises a first tube body 101 and a second tube body 103 that arranged in sequence from the proximal end to the distal end, wherein the diameter of the first tube body 101 is greater than diameter of the second tube body 103; the first tube body 101 and the second tube body 103 are connected by a transition section 102 as a whole; the central diameter of the transition section 102 is smaller than the diameter of the proximal end of the transition section 102 and the diameter of the distal end of the transition section 102; a plurality of fenestrations 200 are disposed on the first tube body 101 and the transition section 102.

The stent graft of the present invention is divided into three parts, a first tube body 101, a second tube body 103 and a transition section 102, and these three parts are fixedly connected to form a whole or an integrated structure. The whole stent graft appears dumbbell shaped, that is, the central diameter of the transition section 102 is the smallest, besides, the diameter of the first tube body 101 is larger than the diameter of the second tube body 103. The first tube body 101 and the second tube body 103 are respectively isodiametric tubes or non-isodiametric tubes. The isodiametric tube body means that the diameter of the tube body is constant, while the non-isodiametric tube body means that the diameter of the tube body changes from the proximal end to the distal end, and a cone or frustum is preferred. As shown in FIGS. 1-2, in this embodiment, both the first tube body 101 and the second tube body 103 adopt isodiametric tube bodies.

The first tube body 101, the second tube body 103, and the transition section 102 are all composed of tubular covering and annular stents; the annular stent is an annular stent with contour or non-contour waves; the annular stent is a whole-sewn frame or partial-sewn frame. The shape, position and number of the annular stents of the three parts are determined according to the stents structure, especially the shape and length of the corresponding part of the covering.

The transition section 102 comprises three parts in sequence, which are a proximal extension section 102A connected to the first tube body 101, a transition body section 102C, and a distal extension section 102B, wherein the transition body section 102C has the smallest diameter among the three parts. In this embodiment, the first tube body 101 of the stent graft 100 has a diameter of 30 mm and a length of 35 mm, and the total length of the transition section 102 is 40 mm, the diameter of the transition body section 102C is 18 mm, and the diameter of the second tube body 103 is 22 mm and the length of that is 25 mm. The tubular covering is made of a polymer material with good biocompatibility. In this embodiment, a PET film is preferred and the film thickness is 0.07 mm to 0.1 mm. The tubular covering has good mechanical strength and anti-endoleak performance.

The following is a detailed description of the three parts of the tube body:

As shown in FIG. 1, in this embodiment, the first tube body 101 is composed of a tubular covering 115 and a plurality of independent annular stents that are uniformly sewn with spacing on the tubular covering 115 in sequence along the axial direction. The annular stents comprise a bare stent 110 and two fenestrated annular stents 120 arranged in sequence from the proximal end to the distal end of the first tube body 101. The bare stent 110 is located at the proximal end of the stent graft, wherein the wave peak of the bare stent 110 is not sewn on the covering 115, and the wave peak of the bare stent 110 is used to be fixed with the delivery device during assembly. Hereon, the vertical height of the bare stent 110 is 18 mm and the diameter is 30 mm. As shown in FIG. 2, the metal bare stent 110 is in the shape of a tube and is composed of multiple Z-shaped or sine waves; each Z-shaped or sine wave has one peak 111 and one adjacent trough 112, and there is a connecting rod 113 between the peak 111 and the adjacent trough 112.

As shown in FIG. 3, the fenestrated annular stent 120 is composed by a plurality of Z-shaped or sine waves 120A and a fenestration-shaped corrugation 120B, each of Z-shaped or sine wave 120A has a wave peak 111 and an adjacent trough 112, and a connecting rod 113 is arranged between the peak 111 and adjacent trough 112, whose structure is same as the bare stent 110; the fenestration-shaped corrugation 120B has two peaks 121 and one trough 122, fenestration-shaped corrugation 120B is located between the two peaks 111 of Z-shaped or sine wave 120A. There are two connecting rods 123 at the peaks 121 and the trough 122 of the fenestration-shaped corrugation 120B, and there are two connecting rods 124 between the peaks 121 and two peaks 111 of the Z-shaped or sine wave 120A. The fenestrated annular stent 120 is woven from a super-elastic nickel-titanium wire with a wire diameter ranging from 0.2 to 0.5 mm. In this embodiment, 0.45 mm is preferred; the number of peaks is set to 6, and the vertical height of the fenestrated annular stent 120 is 15 mm There is one connecting steel sleeve 114 on the fenestrated annular stent 120; the two ends of the nickel-titanium wire are inside the connecting steel sleeve 114, and then the two ends of the nickel-titanium wire are fixed inside the steel sleeve by mechanical compaction or weld. There are two loops of the fenestrated annular stents 120, which are uniformly arranged on the first tube body 101, and the fenestration-shaped corrugation 120B reserves enough space for the disposing the fenestration 200.

As shown in FIG. 2-3, the bare stents 110 and the two fenestrated annular stent 120 are each woven from a superelastic nickel-titanium wire, and the diameter of the nickel-titanium wire ranges from 0.2-0.5 mm, preferably a nickel-titanium wire with a diameter of 0.45 mm in this embodiment, and the number of Z-shaped or sine waves is six. The bare stent 110 and the two fenestrated annular stents 120 each have a connecting steel sleeve 114. The two ends of the nickel-titanium wire are inside the connecting steel sleeve 114, and then the two ends of the nickel-titanium wire are fixed inside the steel sleeve by mechanical compaction or weld. The bare stent 110 and the two fenestrated annular stents 120 are each fixed on the outer surface of the covering material by using a sewing process, so as to keep the whole stent graft with good resilience.

Figure 4:
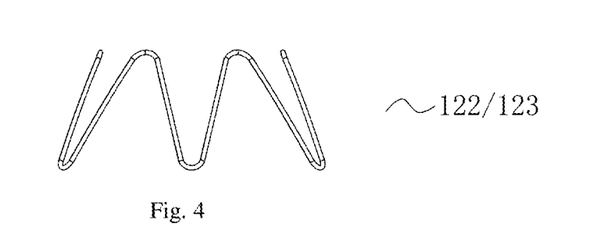
FIG. 4 is a schematic structural view of a conic annular stent in the transition section of Embodiment 1 of the present invention.

As shown in FIG. 1, the transition section 102 comprises a proximal extension section 102A connected to the first tube body 101, a distal extension section 102B connected to the second tube body 103, and a transition body section 102C, and the transition body section 102C has the smallest diameter among the three parts, wherein the proximal extension section 102A and the distal extension section 102B have a tapered structure, and the transition body section 102C has a straight cylindrical structure with a vertical height of 10 mm and a diameter of 18 mm. An annular stent 122 is arranged on the proximal extension section 102A, and an annular stent 123 is arranged on the distal extension section 102B, as shown in FIGS. 1, 4, the shape of both the annular stent 122 and the annular stent 123 are tapered, whose size inosculates with the size of the tapered proximal extension section 102A and the tapered distal extension section 102B. As shown in FIG. 1, the annular stent 121 arranged at the transition body section 102C is an isodiametric annular stent.

As shown in FIG. 1, the tubular covering 125 of the transition section 102 is a dumbbell-shaped, the tubular covering 125 located at the proximal extension section 102A and the distal extension section 102B is tapered, which located at the transition body section 102C is a straight cylinder. The parts of the tubular covering 125 are sewn together or in an integrated structure. The diameter of the straight cylindrical transition body section 102C of the stent graft of the present invention near the renal artery is the smallest diameter in the stent graft, which can provide rich space for implanting the renal artery branch stent, and will not squeeze the branch vessel stent. The diameter of the proximal extension section 102A of the proximal end of transition section 102 gradually increases from a position connected to the transition body section 102C until comparable to the diameter of the first tube body 101; the diameter of the distal extension section 102B of the distal end of transition section 102 gradually increases from a position connected to the transition body section 102C until comparable to the diameter of the second tube body 103. As shown in FIG. 1, the second tube body 103 is composed of a tubular covering 135 and a plurality of independent annular stents 131 that are uniformly sewn with spacing on the tubular covering 135 in sequence along the axial direction. In this embodiment, one annular stent 131 is arranged.

Figure 5:
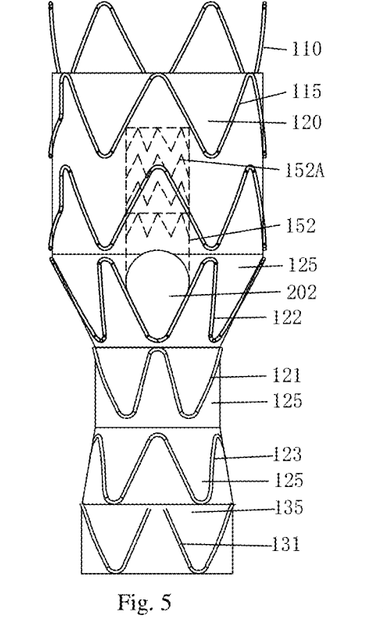
FIG. 5 is a schematic side structural view of a stent graft according to the Embodiment 1 of the present invention.

As shown in FIGS. 1 and 5, the first tube body 101 and the transition section 102 are arranged with multiple fenestrations 200. The fenestrations 200 comprise front wall fenestrations 201 and side wall fenestrations 202; wherein the front wall fenestrations 201 are shown in FIG. 1, the front wall fenestrations 201 disposed on the front wall of the covering, and at least two front wall fenestrations 201 are arranged; all front wall fenestrations 201 are generally arranged sequentially in the axial direction; since the front wall fenestrations are used to connect the celiac trunk artery and the superior mesenteric artery correspondingly, for the position of celiac trunk artery and the superior mesenteric artery, preferably two front wall fenestrations 201 are adopted in this embodiment, and preferably the two front wall fenestrations 201 are located on the same axis, that is, the two front wall fenestrations 201 are arranged symmetrically about the same axis. Also according to the position of the stent graft in the abdominal aorta, at least one front wall fenestration 201 is located on the first tube body 101. In this embodiment, two front wall fenestrations 201 are located on the first tube body 101, wherein one is a front wall fenestration 201 arranged at the proximal end of the first tube body 101, and the other is a front wall fenestration 201 arranged in at the middle of the first tube body 101, wherein the front wall fenestration 201 at the proximal end of the first tube body 101 is a groove-shaped structure with an opening, and the groove is a square, U-shaped or semi-circular structure; in this embodiment the U-shaped front wall fenestration 201 is selected. The front wall fenestration 201 in the middle of the first tube body 101 is circular or oval. The opening edge of the front wall fenestration 201 is arranged with a metal ring 130, and the metal ring 130 is preferably round, whose center of the circle is 20 mm away from the end face of the proximal body covering, and the diameter of the circle is about 11 mm, in this embodiment; the metal ring 130 is preferably a radiopaque wire with a wire diameter of 0.35 mm, which is used to display the position of the fenestration during surgery. The U-shaped front wall fenestration 201 has a width of 12 mm and a depth of 12 mm.

As shown in FIG. 5, the side wall fenestration 202 is arranged on the side surface of the covering, the side wall fenestrations 202 are arranged on each of the both side wall surface of the covering, and the two side wall fenestrations 202 are located at the same height.

Figure 6:
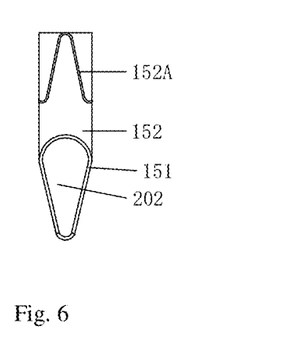
FIG. 6 is a schematic structural view of a fenestration of the side wall according to the Embodiment 1 of the present invention.

As shown in FIGS. 5-6, the side wall fenestration 202 is connected with an embedded tube body 152. The embedded tube body 152 is arranged in the stent graft and extends toward the proximal end of the stent graft. The shape of the side wall fenestration 202 may be a circle, an oval, or other shapes. In this embodiment, the side wall fenestration 202 has a V-shaped structure, and is located at the proximal extension section 102A, and connected to the embedded tube body 152. The side wall fenestration 202 may be directly disposed on the tubular covering 125, or a metal ring 151 for support may be arranged on the edge of the side wall fenestration 202. The shape of the metal ring 151 is the same as the side wall fenestration 202. The embedded tube body 152 extends from the side wall fenestration 202 towards the proximal end of main body stent into the lumen of the first tube body 101, and presents a tubular structure, and embedded tube body 152 of this tubular structure embedded in the inner surface of the first tube body 101. The material of the embedded tube body 152 is a polymer material with good biocompatibility. In this embodiment, a PET film is preferred. A small metal support frame 152A with a Z-wave structure can be arranged on the outer surface of the embedded tube body 152, which can ensure good resilience of the embedded tube body 152. The range of the diameter of the embedded tube body 152 is 6 mm~12 mm, and the length range is 5 mm~20 mm. In this embodiment, the diameter is preferably 8 mm and the length is 12 mm; the wire diameter of the small metal support frame 152A can be selected from a range of 0.2 mm~0.4 mm, and in this embodiment the wire diameter is preferably 0.25 mm.

Figure 7:
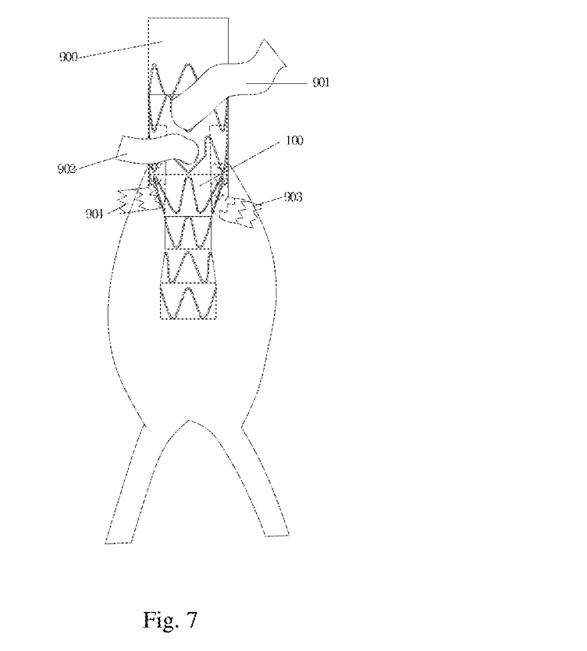
FIG. 7 is a schematic structural view of a stent graft that implanted in the blood vessel according to the Embodiment 1 of the present invention.

As shown in FIG. 7, after the stent graft 100 is implanted into the abdominal artery 900, the front wall fenestrations correspond to the coeliac trunk 901 and the superior mesenteric artery 902, respectively, to ensure the patency of the celiac trunk and superior mesenteric artery, and the two fenestrations 202 located on the side wall of the stent graft 100 are located above the left and right renal arteries 903 and 904, respectively. At this time, if the abdominal aortic aneurysm involves the renal artery, small stent grafts need to be implanted in the left and right fenestrations 202 by means of intraluminal intervention to ensure the patency of the renal artery. In this embodiment, the stent graft 100 has a dumbbell-shaped structure, that is, the diameter of central segment of the transition section of the stent graft 100 is relatively small. After the stent graft 100 is implanted into the diseased abdominal artery, whose transition section is located in the renal artery segment to ensure a larger space between the vessel wall of renal artery and the stents of the transition section of the stent graft, which not only facilitates the approaching of guide wire during the intraluminal intervention of the small stent graft and shortens the operation time, but also ensure having more space after the implantation of the small stent graft, preventing the deformation of the renal artery branch stent caused by the compression of the main body stent after implantation, reducing its irritation to the blood vessel walls, thereby achieving a more ideal intraluminal interventional surgery effect, and better protecting the renal artery and peripheral blood vessels.

The Embodiment 2, this embodiment is an improvement based on Embodiment 1.

Figure 8:
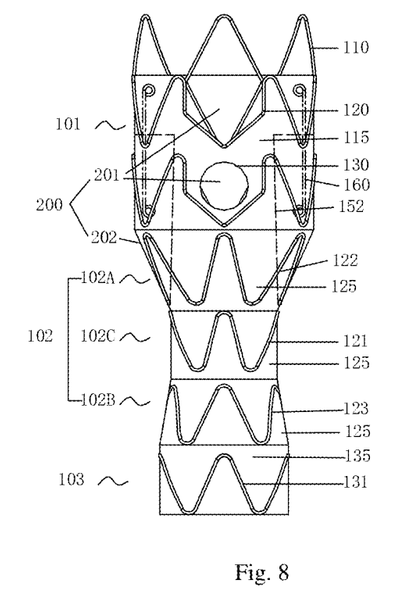
FIG. 8 is a schematic structural view of a stent graft according to the Embodiment 2 of the present invention.
Figure 9:
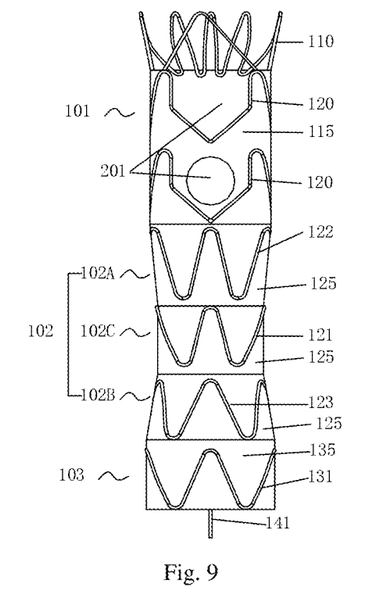
FIG. 9 is a schematic front structural view of a stent graft in the semi-deployed state under restraint according to the Embodiment 2 of the present invention.
Figure 10:
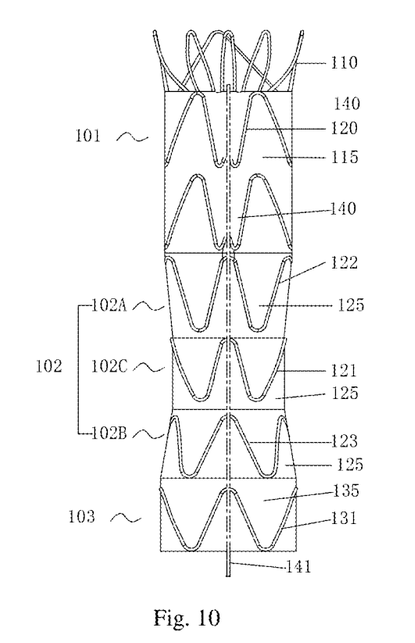
FIG. 10 is a schematic rear structural view of a stent graft in the semi-deployed state under restraint according to the Embodiment 2 of the present invention.

The difference from the Embodiment 1 is that adding a support rod 160 basing on the Embodiment 1. As shown in FIGS. 8-10, at least one support rod 160 arranged along the axial direction is fixed at least to the proximal end of the inner wall surface or the outer wall surface of the covering in the circumferential direction of the covering. The first function of the support rod 160, that is, the most important function is to form a stent in a semi-deployed state, that is, two or more adjacent support rods 160 are drawn close to each other parallel and fixed by a release guide wire 141 passing through, during the drawing process, the support rod 160 can always maintain the flatness of the covering and the stability of the overall structure of the stents. The tubular covering and the annular stents between the support rods 160 are folded to reduce the diameter of the stents, forming a semi-deployed state, and the diameter of stents of semi-deployed state is smaller than the diameter of the blood vessel, so that it can rotate freely and move longitudinally in the blood vessel to adjust the position, facilitating accurate positioning of the stent graft during the release process. As shown in FIGS. 9-10, when the stent graft is in a semi-deployed state under the restraint of the guide wire 141 (on the delivery device), the stents behind the fenestration 200 is still in a restrained state, and the overall diameter of the stents is smaller, and two front wall fenestrations 201 are in the released state, which in the clinical application process, because the stent graft is not fully released it can be conveniently rotated axially and circumferentially in the blood vessel through the delivery system thanks to its smaller overall diameter, which can more quickly and accurately locate the accurate position of the front wall fenestrations 201, so that it can smoothly anastomose with the branch blood vessel and shorten the operation time, resulting in an improvement of the success rate of surgery.

The support rods 160 are arranged along the axis of the tubular covering in the circumferential direction of the tubular covering. The plurality of support rods 160 are preferably arranged axially and symmetrically. There are two types of positional relationship between the support rods 160: one is the support rods 160 are arranged parallel to the central axis of the stents; the other is non-parallel to the central axis of the stents, that is, the support rods 160 are arranged in a shape of a figure eight expressed in Simplified Chinese or a shape of an inverted figure eight expressed in Simplified Chinese, preferably the angle between the support rod 160 and the center axis of the stents is less than 30°. The support rod 160 arranged parallel to the central axis of the stents, FIGS. 9-10 are respectively the front and rear structural schematic views of the stent graft in the semi-deployed state under restraint when the support rods 160 arranged parallel, after the fixing as the figures shown, the diameter of the stents is synchronously reduced. For example, the first tube body 101 and the second tube body 103 are straight cylindrical originally, and in semi-deployed state are also straight cylindrical. The transition section 102 is reduced by the same proportion, and the transition section 102 also maintains a dumbbell-shaped structure. In the second case, the stent graft has a tapered shape with a slightly changed diameter as a whole, and the angle of the tapered angle should not be too large, preventing it from being unable to receive into the sheath. In this embodiment, the support rod 160 is preferably arranged parallel to the central axis of the stents. The number of support rods 160 is generally 2-6, preferably 2-3. When more than two support rods 160 are arranged, all of the support rods 160 are drawn close to each other parallelly and fixed by installing the release guide wire 141 to form a semi-deployed state of the stent graft.

The support rods 160 are arranged at least at the proximal end of the tubular covering of the first tube body 101, which means that the proximal end of the support rods 160 are arranged at the proximal end of the tubular covering of the first tube body 101. The support rods 160 can extend toward the distal end of the stent graft, and its length can be selected as needed. The support rods 160 can extend to the middle of the axial direction of the stent graft, or to the distal end of the axial direction of the stent graft.

As shown in FIG. 8, it is preferable that two support rods 160 are fixed on the inner surface of the tubular covering of the cylindrical structure, and the two support rods 160 are arranged at the proximal end of the rear wall of the tubular between the side wall fenestrations 202, and symmetrically arranged with respect to the central axis of the two front wall fenestrations 201. The distance between two support rods 160 is ⅓ of the circumferential arc length of the first tube body 101 preferably; side wall fenestrations 202 are located at the covering between the front wall fenestrations 201 and the support rods 160, when two support rods 160 are drawn close, the front wall fenestrations 201 and the side wall fenestrations 202 are both in a released state, and will not be covered by the stent graft after being folded. The support rods 160 are distributed at the first tube body 101, and fixed on the inner wall or outer wall of the tubular covering 115 by the processes such as sewing, heat sealing or bonding, preferably by sewing; in the embodiment, the support rods 160 are fixed on the inner wall of the tubular covering 115 by sewing. The material of the support rod 160 is metal or polymer material with a certain support strength, preferably metal material, such as a nickel-titanium alloy wire, with a wire diameter ranging from 0.3 mm to 0.6 mm. In this embodiment, the wire diameter is preferably 0.45 mm.

Figure 11:
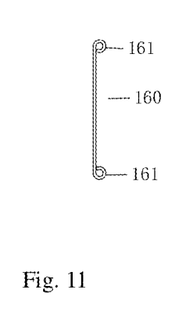
FIG. 11 is a schematic structural view of a support rod according to the Embodiment 2 of the present invention.

The structure of the support rod 160 is shown in FIG. 11, and the support rod 160 shown in the figure is a straight rod structure. At least one fixing point for fixed connection with the covering is arranged on the support rod 160, and the support rod 160 is fixed on the inner or outer wall of the tubular covering by the processes such as sewing, heat sealing or bonding. The fixing point is a connection hole or an opening slot with an opening arranged on the support rod 160. In this embodiment, there are two fixing points on both ends of the support rod 160 respectively. The fixing points in this embodiment are two limit rings 161 with connection holes, which are formed by curling the two ends of the support rod 160, and the diameter of the limit ring 161 ranges from 1.5 mm to 3.5 mm. In this embodiment, the diameter of the limit ring 161 is preferably 2.5 mm. The limit ring 161 is fixed to the proximal end of the tubular covering by sewing to prevent the support rod 160 from sliding off in the axial direction in the stent graft. In addition to the connection hole, the fixing point can also be a non-closed-loop structure, or an opening slot with an opening, for example: bending somewhere in the support rod 160 to form a semi-circular or arc-shaped opening slot, and the support rod 160 cannot move axially after fixed at the opening slot.

In this embodiment, the support rod 160 plays a supporting role in the axial direction, and also serves as a stud during assembly of the stent graft. Fixing the release guide wire to the support rod by connection methods as passing through or winding around, which can not only ensure the stability of the stents during assembly, but also ensure a semi-deployed state of stable circumferential structure after the stent graft is partially released, so that the diameter of the stents in the semi-deployed state is smaller than the diameter of the blood vessel, and the position can be adjusted by free rotation and longitudinal movement in the blood vessel, facilitating an accurate positioning of the stent during the release process.

The rest of the structure is the same as that in Embodiment 1, and will not be repeated here.

The Embodiment 3, this embodiment is an improvement based on Embodiment 1.

Figure 12:
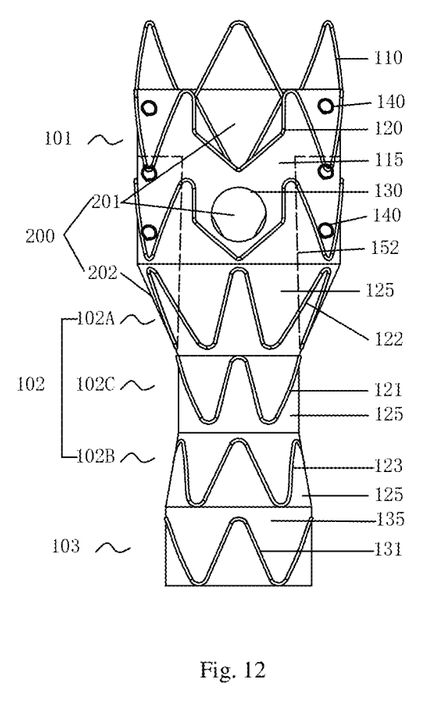
FIG. 12 is a schematic structural view of a stent graft according to the Embodiment 3 of the present invention.
Figure 13:
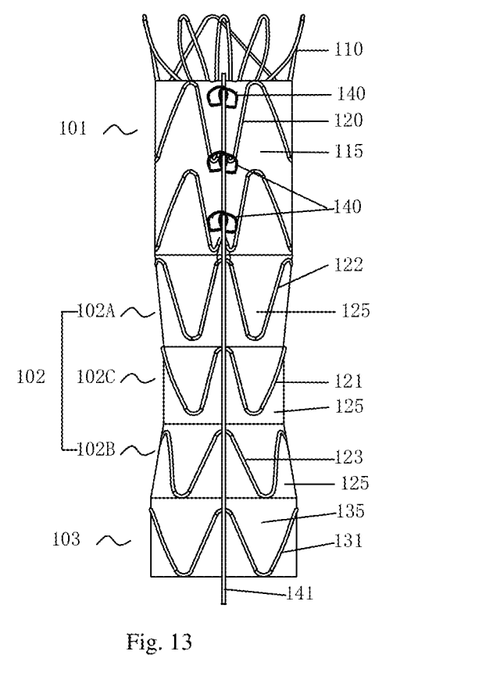
FIG. 13 is a schematic rear structural view of a stent graft in the semi-deployed state under restraint according to the Embodiment 3 of the present invention.

As shown in FIGS. 12-13, the difference from Embodiment 1 is that connectors 140 for a release guide wire 141 to pass through are arranged axially from the proximal end to the distal end on the covering, and the connectors are arranged at least two columns axially with spacing.

The connector 140 is used for the release guide wire 141 to pass through axially, and serving to assist the release guide wire 141 to restrain the stents in the radial direction to form a semi-deployed state, and the structure of the connector 140 needs to meet the above purpose at the same time, so the connector 140 can choose two kinds of structure: a closed-loop structure or an open-loop structure for the release guide wire 141 to pass through or wind around; in the first structure, the closed-loop structure means that the connector 140 has a through hole through which the release guide wire 141 passes, or a through hole or a gap enclosed by the connector 140 cooperation with the covering for the release guide wire 141 to pass through. Specifically, the first embodiment is: the connector 140 is a coil fixed on the outer wall surface of the covering; the second embodiment is: the connector 140 is a piece of wire fixed with a axial spacing, and a gap for the release guide wire 141 to pass through is formed between the fixed wire with spacing and the covering; the third embodiment is: the connector 140 is a through hole directly disposed in the covering;

The open-loop structure is arranged with a limit groove through which the release guide wire 141 passes, that is, the connectors 140 are at least two columns of flexible connection buckles with a limit groove, and the openings of the limit grooves in different columns are arranged in the opposite direction.

In order to prevent the connector from damaging the blood vessel during the release of the stent graft, the connector 140 is a flexible connection buckle arranged on the covering or can be attached on the covering, preferably a biocompatible polymer material, such as polyester, and the material can also choose metal wire.

As shown in FIGS. 12-13, in this embodiment, the connector 140 is a coil with a through hole, and the release guide wire 141 with a wire diameter of 0.5 mm to 1.5 mm can pass through the through hole. In this embodiment, the material of the release guide wire 141 is preferably the nickel-titanium alloy wire, and the wire diameter is 0.5 mm, and the number of connectors 140 is six, and the connectors are uniformly fixed on the covering 120 in two columns, wherein there are three connectors 140 in each column. When assembling, first draw the two columns of connectors 140 together, and the release guide wire 141 fixed on the delivery device passes through the different columns of connectors 140 in sequence. Under the restraint of the release guide wire 141, the stent graft is maintained as a semi-deployed state, and then the stent graft is fully compressed in the sheath of the delivery device. When release, first release the portion of the stent graft that is not restrained by the connectors 140, at this time, the covering between the connectors 140 is still in a restrained state, and the stent graft is not completely released, the overall diameter of the stents is smaller, and two front wall fenestrations 201 are in the released state, which in the clinical application process, because the stent graft is not fully released, it can be conveniently rotated axially and circumferentially in the blood vessel through the delivery system thanks to its smaller overall diameter, which can more quickly and accurately locate the accurate position of the front wall fenestrations 201, so that it can smoothly anastomose with the branch blood vessel and shorten the operation time, resulting in an improvement of the success rate of surgery. After finding the correct release position of the stents, the release guide wire 141 is withdrawn, and the stent graft is completely released and firmly fits in the blood vessel.

The rest of the structure is the same as that in Embodiment 1, and will not be repeated here.

The Embodiment 4, this embodiment is an improvement based on Embodiment 1-3.

Figure 14:
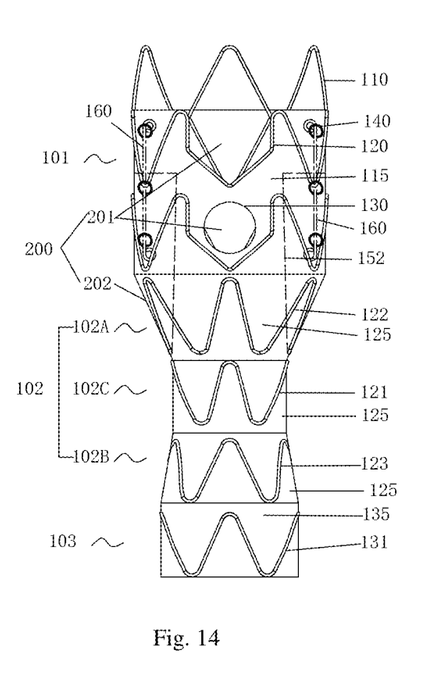
FIG. 14 is a schematic structural view of a stent graft according to the Embodiment 4 of the present invention.
Figure 15:
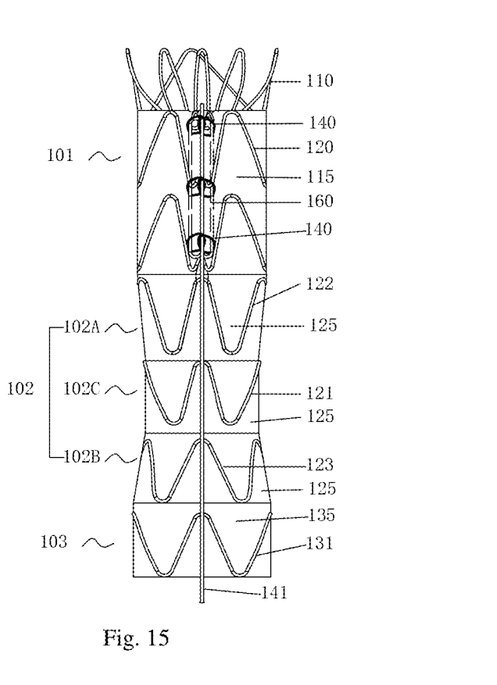
FIG. 15 is a schematic rear structural view of a stent graft in the semi-deployed state under restraint according to the Embodiment 4 of the present invention.

As shown in FIGS. 14-15, the difference from Embodiment 1 is that this embodiment adds the support rod 160 described in Embodiment 2 and the connector 140 described in Embodiment 3 at the same time based on Embodiment 1. That is, the inner wall surface or the outer wall surface of the covering is fixed with at least one axially arranged support rod 160, and the support rod 160 or the covering corresponding to the support rod 160 is arranged with connectors 140 for the release guide wire 141 to pass through.

Wherein, the structure and the position of the supporting rod 160 and the connector 140 on the covering are the same as those in the embodiment 2-3, which will not be repeated here.

The relative position between the supporting rods 160 and the connectors 140 is shown in FIGS. 14-15, and the connectors 140 are arranged on outer wall surface of covering that corresponding to the support rods 160, or on the outer wall surface of the covering around the support rods 160.

As shown in FIGS. 14-15, the number of the connectors 140 in this embodiment is six, which are uniformly divided into two columns and fixed at both ends and central positions of the metal support rods 160.

Figure 16A:
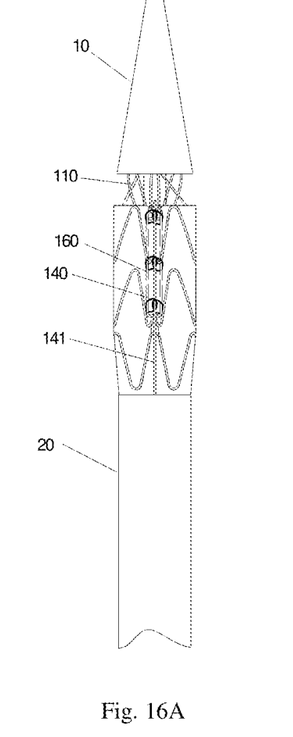
FIG. 16A is a schematic rear structural view of a partial release of the only proximal covering during the release of the stent graft according to the Embodiment 4.
Figure 16B:
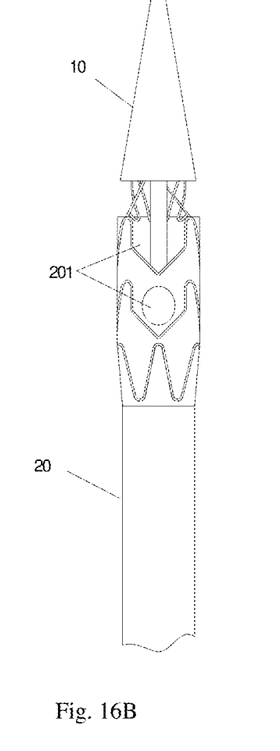
FIG. 16B is a schematic front structural view of a partial release of the only proximal covering during the release of the stent graft according to the Embodiment 4.

As shown in FIG. 16A-16B, when the stent graft is released, the stent graft is in a semi-deployed state under the restraint of the release guide wire 141, and a portion of the stents behind the front wall fenestrations 201 and the side wall fenestrations 201 on the proximal end of the stent graft is still in a restrained state, and the overall diameter of the stents is small, and the U-shaped front wall fenestration 201 and the annular front wall fenestration 201 are in the released state. In the clinical application process, because the stent graft is not fully released, the distal covering is bound in the outer sheath 20 and the proximal bare stent 110 is still bound in the TIP head 10 of the delivery device, and it can be conveniently rotated axially and circumferentially in the blood vessel through the delivery system thanks to its smaller overall diameter, which can more quickly and accurately locate the accurate position of the front wall fenestrations 201, so that it can smoothly anastomose with the branch blood vessel and shorten the operation time, resulting in an improvement of the success rate of surgery. On the other hand, the support rods 160 can also be used as a stud during the assembly of the stent graft, which can not only ensure the stability of the stents during assembly, but also ensure a semi-deployed state of stable circumferential structure after the stents is partially released, preventing the front wall fenestrations 201 are deformed when the stents is in a semi-assembled or semi-deployed state, resulting in inaccurate positioning.

The rest of the structure is the same as that in Embodiment 1-3, and will not be repeated here.

The Embodiment 5, this embodiment is an improvement based on Embodiment 1-4.

Figure 17:
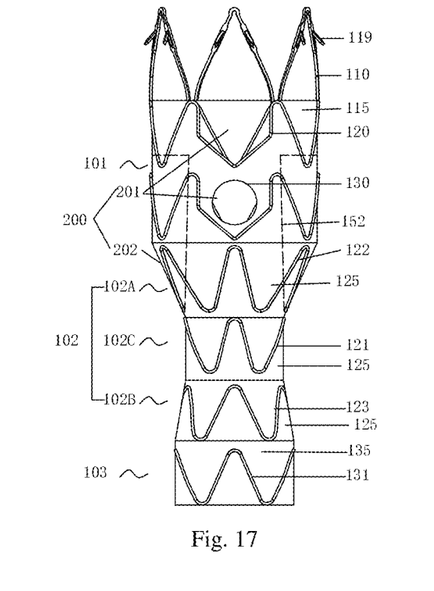
FIG. 17 is a schematic structural view of a stent graft according to the Embodiment 5 of the present invention.
Figure 18:
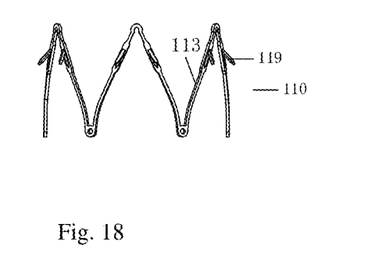
FIG. 18 is a schematic structural view of a bare stent with barbs according to the Embodiment 5 of the present invention.

The difference between this embodiment and Embodiments 1-4 is that the bare stent 110 connected to the first tube body 101 presents a structure with barbs 119. As shown in FIGS. 17-18, the bare stent 110 with barbs 119 has the same main structure as the bare stent 110 of the first tube body 101 in Embodiment 1, except that the bare stent 110 is arranged with barbs 119 that are folded outward, and the free end of the barb 119 faces the distal end of the stent. The bare stent 110 is a laser-cutting stent, and the barbs 119 are an integral structure formed by longitudinally cutting along the connecting rod 113 of the bare stent 110 and folding outward, specifically there are barbs 119 at the position near the peaks of the connecting rods 113. The bare stent 110 with barbs 119 may further provide anchoring of the stent graft.

The rest of the structure is the same as that in Embodiment 1-4, and will not be repeated here.

The invention claimed is:

1. A stent graft used for interventional treatment of abdominal aortic disease, comprising a tubular body composed of a tubular covering and a plurality of annular stents, wherein the tubular body comprises a first tube body and a second tube body that arranged in sequence from the proximal end to the distal end, and the diameter of the first tube body is greater than the diameter of the second tube body;

the first tube body and the second tube body are connected by a transition section as a whole; the diameter at central part of the transition section is smaller than the diameter of the proximal end and the diameter of the distal end of the transition section; the transition section comprises a proximal extension section connected to the first tube body;

a plurality of fenestrations are disposed on the first tube body and the transition section; the plurality of fenestrations comprise at least two front wall fenestrations arranged on the front wall of the covering and side wall fenestrations arranged on each of two side wall surfaces of the covering; wherein at least one front wall fenestration is arranged on the first tube body; the side wall fenestrations are arranged on the proximal extension section, the side wall fenestrations face towards the distal end of the transition section;

the stent graft further comprises at least one embedded tube body; each of the at least one embedded tube body is coupled to a corresponding side wall fenestration; each of the at least one embedded tube body extends from the corresponding side wall fenestration towards the proximal end of the tubular body, and is embedded in an inner surface of the first tube body; and wherein at an inner wall surface or at an outer wall surface of the covering, a plurality of support rods arranged in the axial direction are fixed to at least the proximal end of the first tube body along the circumferential direction of the covering, and when two or more adjacent support rods are drawn close to each other parallel, the two or more adjacent support rods always maintain flatness of the covering and stability of an overall structure of the stent graft.

2. The stent graft used for interventional treatment of abdominal aortic disease according to claim 1, wherein all of the front wall fenestrations are on the same axis, the two side wall fenestrations are located at the same height.

3. The stent graft used for interventional treatment of abdominal aortic disease according to claim 1, wherein the plurality of support rods comprise two support rods, the two support rods are arranged at a proximal end of a rear wall of the covering between the side wall fenestrations, and symmetrically arranged with respect to a central axis of the at least two front wall fenestrations, and when two support rods are drawn close, the front wall fenestrations and the side wall fenestrations are both in a released state.

4. The stent graft used for interventional treatment of abdominal aortic disease according to claim 3, wherein the plurality of support rods are arranged parallel to the central axis of the stents; or the plurality of support rods are arranged in a truncated V-shape or in an inverted truncated V-shape.

5. The stent graft used for interventional treatment of abdominal aortic disease according to claim 1, wherein at least one fixing point for fixed connection with the covering is arranged on the plurality of support rods, and the fixing point is a connection hole or an opening slot with an opening arranged on the plurality of support rods.

6. The stent graft used for interventional treatment of abdominal aortic disease according to claim 1, wherein connectors for a release guide wire to pass through, are arranged axially from the proximal end to the distal end on the covering, and the connectors are arranged at least two columns axially at interval; the connector is configured for the release guide wire to pass through axially, and serving to assist the release guide wire to restrain the stents in the radial direction to form a semi-deployed state.

7. The stent graft used for interventional treatment of abdominal aortic disease according to claim 6, wherein the connector is a closed-loop structure or an open-loop structure for the release guide wire to pass through or wind around; the closed-loop structure is a through hole on the connector for the release guide wire to pass through, or a through hole or a gap surrounded by the connector cooperated with the covering for the release guide wire to pass through, and the open-loop structure has a limit groove for the release guide wire to pass through.

8. The stent graft used for interventional treatment of abdominal aortic disease according to claim 7, wherein the connector with the closed-loop structure is a coil fixed on the outer wall surface of the covering; or, the connector with the closed-loop structure is a piece of wire fixed axially with spacing, and a gap that formed between the wire and the covering for the release guide wire to pass through; or the connector with the closed-loop structure is a through hole formed in the covering; or, the connectors with the open-loop structure are at least two columns of flexible connection buckles with a limit groove, the openings of the limit grooves in different columns arranged in the opposite direction.

9. The stent graft used for interventional treatment of abdominal aortic disease according to claim 6, wherein the connectors are arranged at a proximal end of a rear wall of the tubular covering between the side wall fenestrations.

10. The stent graft used for interventional treatment of abdominal aortic disease according to claim 6, wherein the connector is a coil fixed on the outer wall surface of the covering; or the connector is a piece of wire fixed with a axial spacing, and a gap for the release guide wire to pass through is formed between the fixed wire with spacing and the covering; or the connector is a through hole directly disposed in the covering.

11. The stent graft used for interventional treatment of abdominal aortic disease according to claim 1, wherein a plurality of support rods axially arranged are fixed at the inner wall surface or the outer wall surface of the covering, and a connector for the release guide wire to pass through is arranged at the plurality of support rods or the covering corresponding to the plurality of support rods.

12. The stent graft used for interventional treatment of abdominal aortic disease according to claim 1, wherein a bare stent is arranged at the proximal end of the first tube body, and a plurality of barbs folded outwards are arranged at the bare stent, wherein the free end of the barbs are towards the distal end of the stent.

13. The stent graft used for interventional treatment of abdominal aortic disease according to claim 1, wherein the transition section comprises three parts in sequence, which are the proximal extension section connected to the first tube body, a transition body section, and a distal extension section, wherein the transition body section has the smallest diameter among the three parts.

14. The stent graft used for interventional treatment of abdominal aortic disease according to claim 13, wherein the transition body section is an isodiametric structure, and the proximal extension section and the distal extension section are non-isodiametric structures; the proximal extension section and the distal extension section are tapered.

15. The stent graft used for interventional treatment of abdominal aortic disease according to claim 1, wherein the side wall fenestrations are directly disposed on the tubular covering; or a metal ring for support is arranged on an edge of each of the side wall fenestrations; a shape of the metal ring is the same as a shape of the side wall fenestrations; each of the side wall fenestrations has a V-shaped structure.

16. The stent graft used for interventional treatment of abdominal aortic disease according to claim 1, wherein the stent graft further comprises a plurality of support rods arranged in the axial direction; the plurality of support rods are fixed at an inner wall surface or an outer wall surface of the tubular covering; the plurality of support rods are configured to be drawn close to each other parallel and fixed by a release guide wire passing through to allow the stent graft to be in a semi-deployed state; a diameter of stent graft in the semi-deployed state is smaller than a diameter of a blood vessel.

17. The stent graft used for interventional treatment of abdominal aortic disease according to claim 16, wherein the side wall fenestrations are located at the tubular covering between the front wall fenestrations and the plurality of support rods; when the stent graft is in the semi-deployed state, the front wall fenestrations are released and exposed.

18. The stent graft used for interventional treatment of abdominal aortic disease according to claim 16, wherein the plurality of support rods are arranged at a proximal end of a rear wall of the tubular covering between the side wall fenestrations.

19. The stent graft used for interventional treatment of abdominal aortic disease according to claim 1, wherein the annular stents comprise two fenestrated annular stents arranged in the first tube body, the fenestrated annular stent is composed by a plurality of Z-shaped or sine waves and a fenestration-shaped corrugation, the fenestration-shaped corrugation reserves enough space for the disposing the at least two front wall fenestrations, each of Z-shaped or sine wave comprises a wave peak and an adjacent trough, a first connecting rod is arranged between the peak and the adjacent trough of the Z-shaped or sine wave, the fenestration-shaped corrugation is located between two circumferentially adjacent peaks of the Z-shaped or sine wave, the fenestration-shaped corrugation comprises two peaks and one trough, the two peaks of the fenestration-shaped corrugation are coupled to the trough of the fenestration-shaped corrugation by two second connecting rods, respectively, and the two peaks of the fenestration-shaped corrugation are coupled to the two circumferentially adjacent peaks of the Z-shaped or sine wave by two third connecting rods.

* * * * *